(12) United States Patent
Lou

(10) Patent No.: US 11,331,061 B2
(45) Date of Patent: May 17, 2022

(54) IMAGING OF PHOTON-COUNTING CT SYSTEM

(71) Applicant: Shanghai Neusoft Medical Technology Co., Ltd., Shanghai (CN)

(72) Inventor: Shanshan Lou, Shanghai (CN)

(73) Assignee: Shanghai Neusoft Medical Technology Co., Ltd., Shanghai (CN)

( * ) Notice: Subject to any disclaimer, the term of this patent is extended or adjusted under 35 U.S.C. 154(b) by 0 days.

(21) Appl. No.: 17/030,014

(22) Filed: Sep. 23, 2020

(65) Prior Publication Data
US 2021/0137473 A1    May 13, 2021

(30) Foreign Application Priority Data
Nov. 11, 2019   (CN) .......................... 201911094472.7

(51) Int. Cl.
A61B 6/00    (2006.01)
A61B 6/03    (2006.01)

(52) U.S. Cl.
CPC ............ *A61B 6/4241* (2013.01); *A61B 6/032* (2013.01); *A61B 6/4266* (2013.01); *A61B 6/58* (2013.01)

(58) Field of Classification Search
CPC ..... A61B 6/4241; A61B 6/032; A61B 6/4266; A61B 6/58
See application file for complete search history.

(56) References Cited

U.S. PATENT DOCUMENTS

| 7,330,578 B2* | 2/2008 | Wang ...................... G06T 15/08 345/419 |
| 2013/0243298 A1* | 9/2013 | Bredno ................. G06T 11/008 382/131 |
| 2013/0251228 A1* | 9/2013 | Polster ................... A61B 6/505 382/131 |

(Continued)

FOREIGN PATENT DOCUMENTS

WO    WO 2016076767    5/2016

OTHER PUBLICATIONS

EP Extended Search Report in European Appln. No. 20202176.2, dated Mar. 12, 2021, 9 pages.

(Continued)

*Primary Examiner* — Blake C Riddick
(74) *Attorney, Agent, or Firm* — Fish & Richardson P.C.

(57) ABSTRACT

Imaging methods, imaging apparatuses and image processing devices are provided. In one aspect, an imaging method includes: scanning a subject to obtain a photon-counting sequence output by a photon-counting detector of a photon-counting CT system; determining, by using a photon-counting model and the photon-counting sequence, a target material distribution parameter value of the subject, and performing imaging based on the target material distribution parameter value. The photon-counting model is created by at least one of a charge sharing model, an energy resolution model, or a pulse pileup model. The charge sharing model is configured to eliminate energy spectrum distortion and counting loss caused by charge sharing. The energy resolution model is configured to eliminate energy spectrum distortion and counting loss caused by energy resolution. The pulse pileup model is configured to eliminate energy spectrum distortion and counting loss caused by pulse pileup.

20 Claims, 3 Drawing Sheets

(56) References Cited

U.S. PATENT DOCUMENTS

| | | | | |
|---|---|---|---|---|
| 2014/0314211 | A1* | 10/2014 | Zou | A61B 6/482 |
| | | | | 378/207 |
| 2015/0160355 | A1 | 6/2015 | Wang et al. | |
| 2016/0070008 | A1* | 3/2016 | Cao | A61B 6/032 |
| | | | | 378/5 |
| 2016/0195623 | A1* | 7/2016 | Wang | G01T 1/171 |
| | | | | 250/370.09 |
| 2016/0203620 | A1 | 7/2016 | Zou et al. | |
| 2017/0273640 | A1* | 9/2017 | Danielsson | A61B 6/5205 |
| 2018/0025512 | A1* | 1/2018 | Zhu | G01R 33/5608 |
| | | | | 382/131 |
| 2018/0211419 | A1* | 7/2018 | Zhu | G06T 7/11 |

OTHER PUBLICATIONS

Wang et al., "MicroCT with energy-resolved photon-counting detectors," IOP Publishing, Physics in Medicine and Biology, Apr. 5, 2011, 56(2011):2791-2816, doi:10.1088/0031-9155/56/9/011.

* cited by examiner

IMAGING OF PHOTON-COUNTING CT SYSTEM

CROSS REFERENCE TO RELATED APPLICATIONS

This application claims priority to Chinese Patent Application No. 201911094472.7 filed on Nov. 11, 2019, the entire content of which is incorporated herein by reference.

TECHNICAL FIELD

The present disclosure relates to the field of medical imaging technology, and more particularly, to imaging methods, imaging apparatuses and image processing devices.

BACKGROUND

A CT (Computed Tomography) system includes an X-ray source (such as a ball tube) and a detector. The X-ray source is configured to emit X-ray beams. After attenuation by a subject, the X-ray beams are received by the detector and converted into signal recognized by a computing system for image reconstruction.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (MRI), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MRI, LINAC, and PET products, have led China to become a global high-end medical equipment producer. As an integrated supplier with extensive experience in large medical equipment, NMS has been committed to the study of avoiding secondary potential harm caused by excessive X-ray irradiation to the subject during the CT scanning process.

SUMMARY

The present disclosure provides methods, devices, systems and apparatus for imaging in photon-counting CT systems, which can eliminate energy spectrum distortion and counting loss to reduce artifacts in the imaging.

In general, one innovative aspect of the subject matter described in this specification can be embodied in methods that include the actions, including: scanning a subject to obtain a photon-counting sequence outputted by a photon-counting detector of a photon-counting CT system; determining, by using a photon-counting model and the photon-counting sequence, a target material distribution parameter value of the subject, the photon-counting model being created by at least one of a charge sharing model, an energy resolution model, or a pulse pileup model, the charge sharing model being configured to eliminate energy spectrum distortion and counting loss caused by charge sharing, the energy resolution model being configured to eliminate energy spectrum distortion and counting loss caused by energy resolution, and the pulse pileup model being configured to eliminate energy spectrum distortion and counting loss caused by pulse pileup; and performing imaging based on the target material distribution parameter value.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination.

In some embodiments, determining, by using the photon-counting model and the photon-counting sequence, the target material distribution parameter value of the subject includes: adjusting a material distribution parameter value in the photon-counting model; and in response to determining that a difference between a theoretical photon-counting sequence and the photon-counting sequence is a minimum, determining the adjusted material distribution parameter value as the target material distribution parameter value. The theoretical photon-counting sequence is determined by the photon-counting model based on the adjusted material distribution parameter value.

In some embodiments, determining, by using the photon-counting model and the photon-counting sequence, the target material distribution parameter value of the subject includes: adjusting a material distribution parameter value in the photon-counting model; and in response to determining that a probability of a theoretical photon-counting sequence being the photon-counting sequence is highest, determining the adjusted material distribution parameter value as the target material distribution parameter value, where the theoretical photon-counting sequence is determined by the photon-counting model based on the adjusted material distribution parameter value.

In some embodiments, the actions further include: determining a tube emission energy spectrum corresponding to an exposure voltage, an exposure current, and an exposure time; and for each of sub-detectors of the photon-counting detector under each scanning view, determining an attenuation length of rays passing through a shape filter of the photon-counting CT system as a first attenuation length, where the rays enter into the sub-detector after passing through the subject under the scanning view; for each voxel of the subject, determining an attenuation length of the rays passing through the voxel as a second attenuation length; and determining an incident ray energy spectrum of the sub-detector under the scanning view based on the tube emission energy spectrum, the first attenuation length, and the second attenuation length and a material distribution parameter value of each voxel of the subject.

In some embodiments, the actions further include: for each of the sub-detectors of the photon-counting detector under each scanning view, determining the charge sharing model based on the incident ray energy spectrum; determining the energy resolution model based on the charge sharing model; determining the pulse pileup model based on the energy resolution model; determining a counting energy spectrum based on the pulse pileup model; and creating the photon-counting model based on the counting energy spectrum.

In some embodiments, the incident ray energy spectrum of the sub-detector under the scanning view is represented by:

$$S_{ij}(E_0) = S_0(E_0)\exp(-L_{ij}\mu_f(E_0) - \Sigma_{l=1}^N a_{ijl}\mu_l(E_0)),$$

where $S_{ij}(E_0)$ represents an incident ray energy spectrum of a j-th sub-detector under an i-th scanning view; $E_0$ represents an energy of an incident photon; $S_0(E_0)$ represents the tube emission energy spectrum corresponding to the exposure voltage, the exposure current and the exposure time; i represents a serial number of the scanning view; j represents a serial number of the sub-detector; $\mu_f(E_0)$ represents an attenuation coefficient curve of the shape filter; $L_{ij}$ represents the first attenuation length; l represents a serial number of the voxel; $a_{ijl}$ represents the second attenuation length; $\mu_l(E_0)$ represents a material distribution parameter value of the voxel l; and N represents a number of voxels obtained after dividing the subject.

In some embodiments, the charge sharing model is represented by:

$$S_{CS}(E_1) = \mathcal{F}_{CS}(S_{ij}) = \int_0^\infty S_{ij}(E_0) R_{CS}(E_1|E_0) dE_0,$$

where $S_{CS}(E_1)$ represents a charge sharing distortion spectrum; $E_1$ represents an energy of a detected photon under an effect of charge sharing; $\mathcal{F}_{CS}$ represents a mapping relationship between $S_{ij}(E_0)$ and $S_{CS}(E_1)$; and $R_{CS}(E_1|E_0)$ represents a response function of charge sharing energy spectrum.

In some embodiments, the energy resolution model is represented by:

$$S_{ER}(E_2) = \mathcal{F}_{ER}(S_{CS}) = \int_0^\infty S_{CS}(E_1) R_{ER}(E_2|E_1) dE_1,$$

where $S_{ER}(E_2)$ represents an energy resolution spectrum; $E_2$ represents an energy of the detected photon under an effect of energy resolution; $\mathcal{F}_{ER}$ represents a mapping relationship between $S_{CS}(E_1)$ and $S_{ER}(E_2)$; and $R_{ER}(E_2|E_1)$ represents a response function of the energy resolution spectrum.

In some embodiments, the pulse pileup model is represented by:

$$S_{PP}(E_3) = \mathcal{F}_{PP}(S_{ER}) N_0 (1-DLR) \Sigma_{m=0}^M P(m) \cdot \Omega(E_3|m, S_{ER}(E_2)),$$

where $S_{PP}(E_3)$ represents a pulse pileup distortion spectrum; $E_3$ represents an energy of the detected photon under an effect of pulse pileup; $\mathcal{F}_{PP}$ represents a mapping relationship between $S_{ER}(E_2)$ and $S_{PP}(E_3)$; $N_0$ represents a total number of incident photons in the i-th scanning view; DLR represents a count loss rate; m represents an order of the pulse pileup; M represents the maximum order of the pulse pileup under the i-th scanning view; P(m) represents a probability that a counted event is an m-order pulse pileup under the i-th scanning view; and $\Omega(E_3|m, S_{ER}(E_2))$ represents a spectral density function of the m-order pulse pileup.

In some embodiments, the photon-counting model is represented by:

$$N_{ijk} = \int_{E_k}^{E_{k+1}} \tilde{S}_{ij}(E_3) dE_3$$

$$\tilde{S}_{ij}(E_3) = \mathcal{F}[S_{PP}(E_3)],$$

where $\tilde{S}_{ij}(E_3)$ represents a counting energy spectrum recorded by the j-th sub-detector under the i-th scanning view; $\mathcal{F}$ represents a mapping relationship between $S_{PP}(E_3)$ and $\tilde{S}_{ij}(E_3)$; $N_{ijk}$ represents a number of detected photons within an energy range $E_k$ to $E_{k+1}$ detected by the j-th sub-detector under the i-th scanning view; k represents a serial number of the energy range; $E_k$ represents an energy lower limit of the energy range k; and $E_{k+1}$ represents an energy upper limit of the energy range k.

In some embodiments, the target material distribution parameter value includes one of: a target voxel attenuation coefficient; and a target mass density of voxel tissue component.

In some embodiments, the actions further include: for each of sub-detectors of the photon-counting detector, performing energy correction on a memory threshold stored in a memory of the sub-detector using a predetermined correction table, where the sub-detector is configured to count photons with the memory threshold. The action can also include: determining the predetermined correction table using radioisotope.

The details of one or more examples of the subject matter described in the present disclosure are set forth in the accompanying drawings and description below. Other features, aspects, and advantages of the subject matter will become apparent from the description, the drawings, and the claims. Features of the present disclosure are illustrated by way of example and not limited in the following figures, in which like numerals indicate like elements.

DETAILED DESCRIPTION

Figure 1:
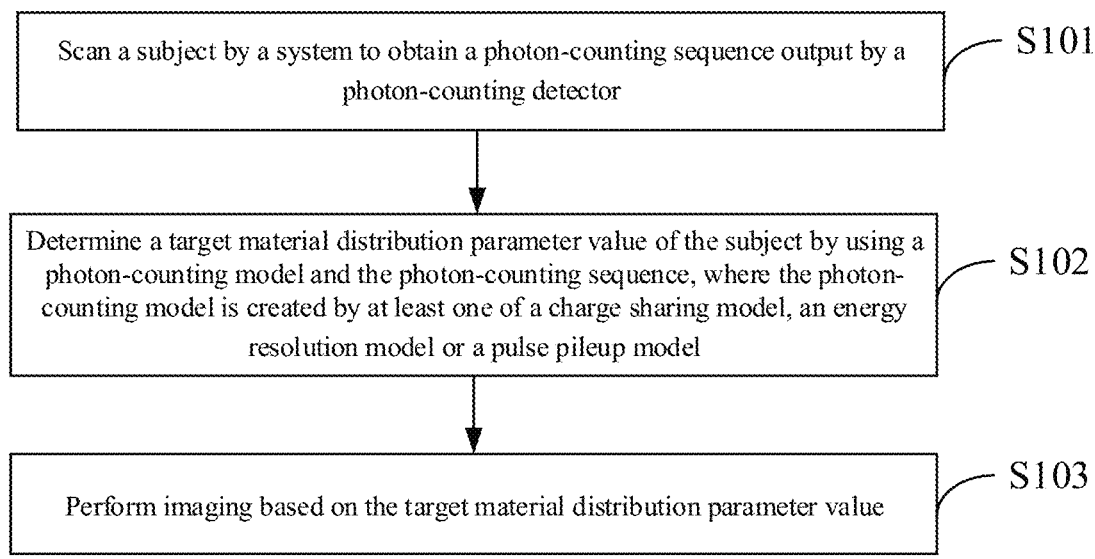
FIG. 1 is a flowchart illustrating a process of an imaging method according to one or more examples of the present disclosure.

According to the different physical mechanisms and output signal acquisition modes, a detector of a CT system can include an energy-integrating detector or a photon-counting detector. The energy-integrating detector is configured to acquire a total energy integral signal of X-ray beams to implement the detection of X-ray information, and has no ability of energy spectrum resolution. The photon-counting detector is configured to convert the energy information of the single incident photon into a pulse signal, and identify the energy information of the single incident photon based on the pulse height of the pulse signal. Thus, the photon-counting detector has the advantage of energy resolution. The energy spectrum imaging of different energy ranges can be implemented by counting photons in different energy ranges. Because different tissues or materials have different attenuation coefficients for photons of the same energy, energy spectrum imaging by photon-counting can reflect more detailed information of the subject, such as a region of interest of the scanned object or human tissues.

However, the photon-counting detector itself has some shortcomings. When these shortcomings are reflected in the acquired data, these shortcomings can include energy spectrum distortion and counting loss. Energy spectrum distortion refers to the differences between the energy spectrum recorded by the photon-counting detector and the incident energy spectrum during the scanning process. These differences include the red shift, blue shift and broadening of the energy spectrum. Counting loss refers to a case that when the incident counting rate of photons (the number of photons incident to a sub-detector per unit time) is greater than a threshold, the number of photons recorded by the sub-detector of the photon-counting detector is less than the number of incident photons. Energy spectrum distortion and counting loss are caused by charge sharing, pulse pileup and energy resolution during the detection process of the photon-counting detector.

Charge sharing refers to a phenomenon in which some charges are detected by the adjacent sub-detectors after the incident photon interacts with the photon-counting detector to generate an electric current carrier, thereby resulting in the counting of the single incident photon occurred in different sub-detectors. Charge sharing may cause red shift of energy spectrum.

Energy resolution reflects the capability of photon-counting detector to accurately distinguish the energy of the incident photon. For the photon-counting detector, even if photons with the same energy are incident in the same sub-detector, the results of energy discrimination for the photons are a changeable value within a particular range. The energy resolution may cause the energy spectrum broadening. Under ideal conditions, each sub-detector can accurately identify the energy of the incident photon, and the detected energy spectrum is basically consistent with the input energy spectrum. But in practice, for each sub-detector, due to the influence of energy resolution, the detected energy spectrum may be widened relative to the input energy spectrum.

Pulse pileup refers to a phenomenon in which when the time interval of the incident photons successively incident on the sub-detector is less than the dead time, the photon-counting detector cannot distinguish each incident photon, and thus the pulse signals generated by adjacent incident photons are superimposed to produce a count together. Pulse pileup may cause counting loss and energy distortion, such as blue shift of energy spectrum.

These shortcomings of the photon-counting detector may cause artifacts in the subsequent image reconstruction process. To eliminate the artifacts caused by these shortcomings, the present disclosure provides an imaging method that can be applied to a photon-counting computed tomography (CT) system (hereinafter referred to as a system), in which a photon-counting detector is installed.

FIG. 1 is a flowchart illustrating a process of an imaging method according to one or more examples of the present disclosure. The process can be performed by a photon-counting CT system. As shown in FIG. 1, the process includes the following steps 101-103.

At step 101, a subject is scanned by the system to obtain a photon-counting sequence output by a photon-counting detector in the system.

Figure 2:
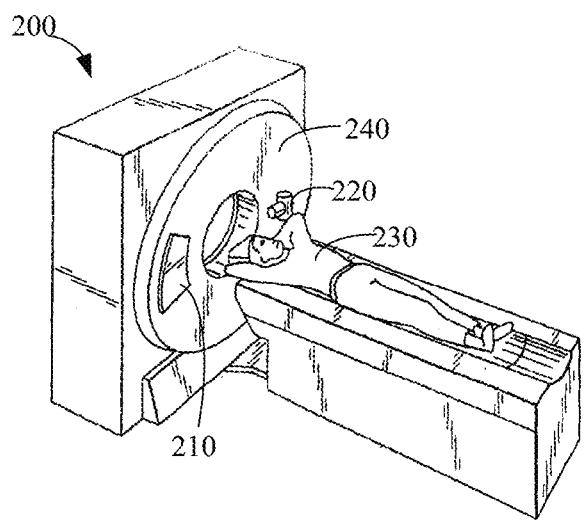
FIG. 2 is a structural diagram of a photon-counting CT system according to one or more examples of the present disclosure.

As shown in FIG. 2, the system 200 includes a photon-counting detector 210, an X-ray source 220 and a gantry 240. The photon-counting detector 210 includes multiple sub-detectors. Each sub-detector has the function of acquiring signals and counting independently. Each sub-detector includes multiple counters, and each counter is configured to count photons within an energy range. For example, each sub-detector includes K counters, by which the photons in K energy ranges are respectively counted. K is an integer greater than 1.

In the scanning process, the X-ray source 220 and the photon-counting detector 210 are rotated around a subject 230 lying on a scanning table of the system 200. The photon-counting detector 210 counts photons in each scanning view. Specifically, each counter in each sub-detector counts photons within the corresponding energy range. After the scanning process is ended, the photon-counting detector 210 outputs the photon-counting sequence. The photon-counting sequence output (or outputted) by the photon-counting detector 210 is a collection of photon counts obtained at each scanning view. That is, the photon-counting sequence output by the photon-counting detector 210 includes all photon counts obtained at each scanning view.

Figure 3:
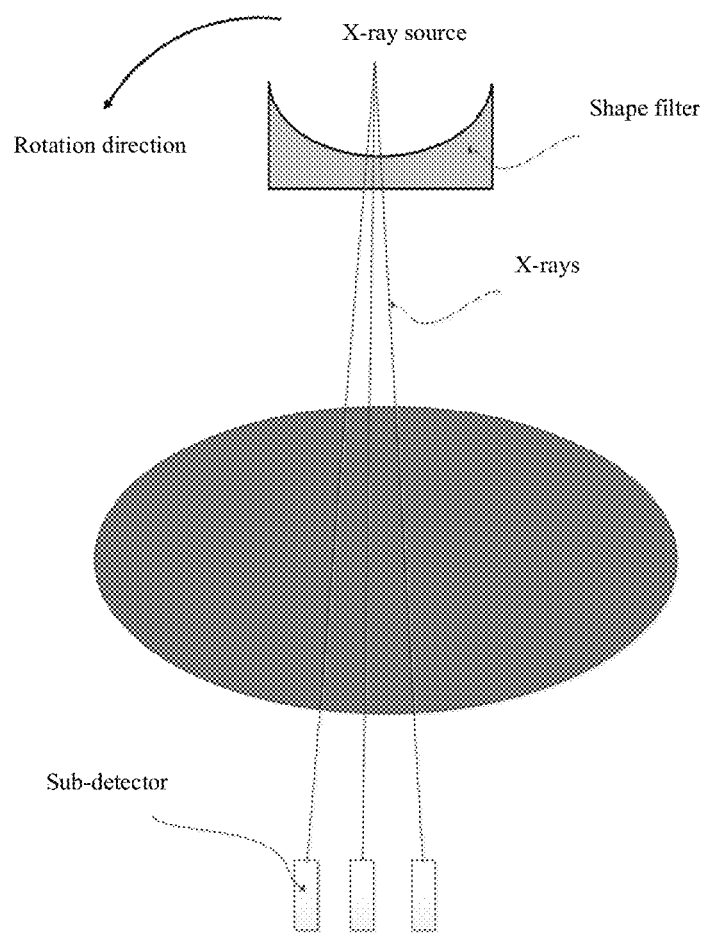
FIG. 3 is a schematic diagram of a scanning process of the photon-counting CT system according to one or more examples of the present disclosure.

There can be multiple ways to determine each scanning view. In an example, each predetermined rotation angle range of the gantry 240 is one scanning view. For example, an initial angle of the X-ray source 220 shown in FIG. 3 is 0 degree and the gantry 240 rotates 5 degrees counterclockwise each time. In this case, the rotation angle range of 0-5 degrees is determined as a first scanning view, the rotation angle range of 5-10 degrees is determined as a second scanning view, the rotation angle range of 10-15 degrees is determined as a third scanning view, . . . , and so on. In another example, an angle range corresponding to each predetermined rotation time length of the gantry 240 is one scanning view. For example, the gantry 240 rotates 5 seconds(s) counterclockwise each time. In this case, an angle range corresponding to the rotation time length of 0-5 s is determined as a first scanning view, an angle range corresponding to the rotation time length of 5-10 s is determined as a second scanning view, an angle range corresponding to the rotation time length of 10-15 s is determined as a third scanning view, . . . , and so on.

At step 102, a target material distribution parameter value of the subject is determined by using a photon-counting model and the photon-counting sequence, where the photon-counting model is created by at least one of a charge sharing model, an energy resolution model or a pulse pileup model.

In some examples, the photon-counting model is created in advance. The photon-counting model can be created before scanning the subject. The photon-counting model reflects the mapping relationship between photon counts and material distribution parameter values. The target material distribution parameter value is the basis of system imaging. The material distribution parameter value can include material attenuation coefficient or mass density.

The photon-counting model is created by at least one of a charge sharing model, an energy resolution model, or a pulse pileup model. The charge sharing model can be generated based on the charge sharing mechanism and used (or configured) to eliminate the energy spectrum distortion and counting loss caused by the charge sharing. The energy resolution model can be generated based on the energy resolution mechanism and used (or configured) to eliminate the energy spectrum distortion and counting loss caused by the energy resolution. The pulse pileup model can be generated based on the pulse pileup mechanism and used (or configured) to eliminate the energy spectrum distortion and counting loss caused by the pulse pileup.

In some examples, the photon-counting model is created by the charge sharing model. Optionally, the photon-counting model is created by the charge sharing model and the energy resolution model. Optionally, the photon-counting model is created by the charge sharing model, the energy resolution model, and the pulse pileup model.

According to a principle that a theoretical photon-counting sequence determined by the photon-counting model is equal to or similar to the photon-counting sequence output by the photon-counting detector, the material distribution parameter value in the photon-counting model can be adjusted to determine the target material distribution parameter value.

There are multiple ways to determine the target material distribution parameter value. In an example, the photon-counting model includes a material distribution parameter. The system can adjust the material distribution parameter value in the photon-counting model by using the least square method. When a difference between a theoretical photon-counting sequence determined by the photon-counting model based on the adjusted material distribution parameter value and the photon-counting sequence output by the photon-counting detector is a minimum, the adjusted material distribution parameter value is determined as the target material distribution parameter value. In another example, the system can adjust the material distribution parameter value in the photon-counting model by using the maximum likelihood estimation method. When a probability that a theoretical photon-counting sequence determined by the photon-counting model based on the adjusted material distribution parameter value is the photon-counting sequence output by the photon-counting detector is highest, the adjusted material distribution parameter value is determined as the target material distribution parameter value.

In some examples, the material distribution parameter value can be an attenuation coefficient of a voxel (which can also be referred to as a voxel attenuation coefficient). The voxel is obtained by spatial division for the subject, and the voxel attenuation coefficient reflects the attenuation ability of the voxel to the intensity of the X-rays.

In some examples, the voxel attenuation coefficient is equal to the sum of the product of the attenuation coefficient and corresponding mass density of each tissue component of the voxel. For example, if the human body is injected with a contrast agent before scanning, the human tissue (voxels) can include water, calcium, contrast agent, etc., and the voxel attenuation coefficient can be equal to a sum of a product of the attenuation coefficient of water multiplied by the mass density of water, a product of the attenuation coefficient of calcium multiplied by the mass density of calcium, a product of the attenuation coefficient of contrast agent multiplied by the mass density of contrast agent, and any other product. Based on the above expression of voxel attenuation coefficient, it can be determined that the voxel attenuation coefficient depends on the tissue components of the voxel and the mass density of each tissue component of the voxel.

The photon-counting model can be created by using at least one of the charge sharing model, the energy resolution model, or the pulse pileup model. Thus, in the process of determining the material distribution parameter value according to the photon-counting model and the photon-counting sequence output by the photon-counting detector, the influence of at least one of the charge sharing, the energy resolution, or the pulse pileup existing in the photon-counting detector on the material distribution parameter value can be eliminated, thereby ensuring the accuracy of the target material distribution parameter value.

At step 103, imaging is performed based on the target material distribution parameter value.

After determining the target material distribution parameter value, the system can perform the imaging based on the target material distribution parameter value. In the imaging method provided by examples of the present disclosure, not only the attenuation process of X-rays in the subjects, but also the physical process of X-rays being detected in the photon-counting detector can be considered, thereby improving the imaging quality. The system can further include a computer. The computer can be configured to send instructions to control the rotation of the gantry 240 and the movement of the scanning table. The image generated according to the target material distribution parameter value can be displayed on a display device of the computer.

The following examples describe the associated content of the technical solutions of the present disclosure in detail.

Creation of Photon-Counting Model

As an example, the material distribution parameter is taken as the voxel attenuation coefficient, and the photon-counting model is created by a charge sharing model, an energy resolution model and a pulse pileup model. To create the photon-counting model, an incident ray energy spectrum model (may also be referred to as an incident ray energy spectrum) of the photon-counting detector is constructed first. The incident ray energy spectrum model includes the material distribution parameter.

The incident ray energy spectrum model outputs a first result based on the material distribution parameter value; the charge sharing model outputs a second result based on the first result output by the incident ray energy spectrum model; the energy resolution model outputs a third result based on the second result output by the charge sharing model; the pulse pileup model outputs a fourth result based on the third result output by the energy resolution model; and the photon-counting model outputs a photon-counting result (may also be referred to as a theoretical photon-counting sequence) based on the fourth result output by the pulse pileup model.

The incident ray energy spectrum model can be constructed in the following ways.

As shown in FIG. 3, in the scanning process, the X-rays emitted by the X-ray source is firstly emitted to a shape filter, the X-rays are filtered by the shape filter and then emitted to the photon-counting detector after passing through the subject.

The attenuation process of X-rays includes two parts: one is in the shape filter, the other is in the subject. The incident ray energy spectrum of each sub-detector under each scanning view may be represented as formula (1):

$$S(E) = S_0(E) \exp(-\int \mu(\vec{x}, E) dl) \quad (1)$$

where $S(E)$ represents the incident ray energy spectrum of the sub-detector; $S_0(E)$ represents a tube emission energy spectrum corresponding to an exposure voltage, an exposure current and an exposure time; $\vec{x}$ represents a spatial position of the attenuation coefficient of the subject; $E$ represents the incident photon energy; and $\mu(\vec{x}, E)$ represents a relationship between the spatial position of the attenuation coefficient of the subject and the incident photon energy.

The shape of the tube emission energy spectrum is different under different tube voltages. The tube emission energy spectrum is determined under the low tube current (to ensure the pulse pileup ratio is low enough) by an empty scan and a threshold traversal scan. An energy spectrum distribution function and the number of the emitted photons are estimated by normalizing the tube emission energy spectrum. The empty scan refers to a scan performed by the system without a subject. If an energy threshold is set to 20 keV, only photons with energy above 20 keV can be detected by the photon-counting detector. In the threshold traversal scan, multiple energy thresholds are configured, each sub-detector counts photons separately for each energy threshold to obtain respective input energy spectrums corresponding to the energy thresholds. During scanning, the tube emission energy spectrum may be represented as formula (2):

$$S_0(E) = k(U) \cdot I \cdot T \cdot \Omega_U(E) \quad (2)$$

where k(U) represents a constant associated with the tube voltage and is measured separately at each tube voltage; I represents the tube current; T represents the exposure time; and $\Omega_U(E)$ represents an emission energy spectrum distribution function.

Because the material, geometry shape and size of the shape filter are known, the spatial distribution of the attenuation coefficient of the shape filter is known. The spatial distribution of the attenuation coefficient of the subject is to be solved. Assuming that each voxel and each energy range in the subject corresponds to an attenuation coefficient, formula (3) is formulated:

$$\mu_l(E) = \sum_{k=1}^{K} \mu_{lk} \mathcal{J}_{(E_k, E_{k+1}]}(E) \quad (3)$$

where l represents the serial number of the voxel in the subject and corresponds to the spatial position; $\mu_l(E)$ represents the voxel attenuation coefficient of the voxel l; k represents the serial number of the energy range; $E_k$ represents an energy lower limit of the energy range k; $E_{k+1}$ represents an energy upper limit of the energy range k; K represents the maximum number of energy ranges; ($E_k$, $E_{k+1}$] represents a threshold interval corresponding to the k-th energy range; $\mu_{lk}$ represents an attenuation sub-coefficient of the voxel l when the incident photon energy is between ($E_k, E_{k+1}$]; when the incident photon energy is within ($E_k, E_{k+1}$], $\mathcal{J}_{(E_k, E_{k+1}]}$ is equal to 1; and when the incident photon energy is beyond ($E_k, E_{k+1}$], $\mathcal{J}_{(E_k, E_{k+1}]}$ is equal to 0.

According to the above formulas (1) and (3), the incident ray energy spectrum model is represented by formula (4):

$$S_{ij}(E_0) = S_0(E_0) \exp\left(-L_{ij}\mu_f(E_0) - \sum_{l=1}^{N} a_{ijl}\mu_l(E_0)\right) \quad (4)$$

where $S_0(E_0)$ represents a tube emission energy spectrum corresponding to an exposure voltage, an exposure current and an exposure time; $E_0$ represents an energy of the incident photon; i represents the serial number of the scanning view; j represents the serial number of the sub-detector; $S_{ij}(E_0)$ represents the incident ray energy spectrum of the j-th sub-detector under the i-th scanning view; $L_{ij}$ represents a length (may also be referred to as attenuation length) of the rays passing through the shape filter and then transmitting into the j-th sub-detector under the i-th scanning view; $\mu_f(E_0)$ represents the attenuation coefficient curve of the shape filter; l represents the serial number of the voxel; $a_{ijl}$ represents a length (may also be referred to as attenuation length) of the rays passing through the voxel l and then transmitting into the j-th sub-detector under the i-th scanning view; $\mu_l(E_0)$ represents the voxel attenuation coefficient of the voxel l; and N represents the number of voxels obtained after dividing the subject.

After the incident ray energy spectrum model is constructed, the charge sharing model is constructed based on the incident ray energy spectrum model. The charge sharing model is represented by formula (5):

$$S_{CS}(E_1) = \mathcal{F}_{CS}(S_{ij}) = \int_0^\infty S_{ij}(E_0) R_{CS}(E_1|E_0) dE_0 \quad (5)$$

where $S_{CS}(E_1)$ represents a charge sharing distortion spectrum; $E_1$ represents the energy of the recognized photon under the effect of charge sharing; $\mathcal{F}_{CS}$ represents a mapping relationship between $S_{ij}(E_0)$ and $S_{CS}(E_1)$; $R_{CS}(E_1|E_0)$ represents a response function of charge sharing energy spectrum; ∞ represents the maximum energy of photons emitted by the tube. The response function of charge sharing energy spectrum can be determined according to the performance parameters of the photon-counting detector. The performance parameters of the photon-counting detector include the size of the sub-detector, the intensity of the applied electric field, and the semiconductor transport characteristics.

After the charge sharing model is constructed, the energy resolution model is constructed based on the charge sharing model. The energy resolution model is represented by formula (6):

$$S_{ER}(E_2) = \mathcal{F}_{ER}(S_{CS}) = \int_0^{28} S_{CS}(E_1) R_{ER}(E_2|E_1) dE_1 \quad (6)$$

where $S_{ER}(E_2)$ represents an energy resolution spectrum; $E_2$ represents the energy of the photon identified under the effect of energy resolution; $\mathcal{F}_{ER}$ represents a mapping relationship between $S_{CS}(E_1)$ and $S_{ER}(E_2)$; $R_{ER}(E_2|E_1)$ represents a response function of the energy resolution spectrum. The response function of the energy resolution spectrum can be represented by a Gaussian function, and the parameters in the Gaussian function are determined by the physical properties of the photon-counting detector.

After the energy resolution model is constructed, the pulse pileup model is constructed based on the energy resolution model. The pulse pileup model is represented by formula (7):

$$S_{PP}(E_3) = \mathcal{F}_{PP}(S_{ER}) = N_0(1 - DLR) \sum_{m=0}^{M} P(m) \cdot \Omega(E_3 \mid m, S_{ER}(E_2)) \quad (7)$$

where $S_{PP}(E_3)$ represents a pulse pileup distortion spectrum; $E_3$ represents the energy of the photon identified under the effect of pulse pileup; $\mathcal{F}_{PP}$ represents a mapping relationship between $S_{ER}(E_2)$ and $S_{PP}(E_3)$; $N_0$ represents the total number of incident photons in the i-th scanning view; DLR represents the count loss rate, which is affected by the dead time; m represents the order of the pulse pileup; M represents the maximum order of the pulse pileup under the i-th scanning view; P(m) represents a probability that a counted event is the m-order pulse pileup under the i-th scanning view; $\Omega(E_3|m, S_{ER}(E_2))$ represents a spectral density function of the m-order pulse pileup, which is affected by the dead time. The counting loss rate (DLR) can be estimated from the photon-counting rate according to the detector type. The spectral density function of each order pulse pileup can be determined according to a pulse waveform and time interval distribution. The pulse waveform refers to the pulse waveform generated after the single photon is incident into the sub-detector. The time interval distribution refers to the incident time interval of different photons. When two or three photons are incident at the same time in the same dead time, the pulse waveform will be superimposed, so that the energy detected by photon-counting detector is higher than the energy generated by a single photon incident.

After the pulse pileup model is constructed, a counting energy spectrum $\tilde{S}_{ij}(E_3)$ recorded by the j-th sub-detector under the i-th scanning view can be determined according to the pulse pileup model. $\mathcal{F}$ represents a mapping relationship between $S_{PP}(E_3)$ and $\tilde{S}_{ij}(E_3)$. The counting energy spectrum $\tilde{S}_{ij}(E_3)$ is represented by the following formula (8):

$$\tilde{S}_{ij}(E_3) = \mathcal{F}[S_{PP}(E_3)] \tag{8}$$

After determining the counting energy spectrum $\tilde{S}_{ij}(E_3)$, the photon-counting model is created based on the counting energy spectrum $\tilde{S}_{ij}(E_3)$. The photon-counting model is represented by the following formula (9):

$$N_{ijk} = \int_{E_k}^{E_{k+1}} \tilde{S}_{ij}(E_3) dE_3 \tag{9}$$

where $N_{ijk}$ represents the number of the photons within an energy range $E_k$ to $E_{k+1}$ detected by the j-th sub-detector under the i-th scanning view; $\tilde{S}_{ij}(E_3)$ represents the counting energy spectrum recorded by the j-th sub-detector under the i-th scanning view; k represents the serial number of the energy range; $E_k$ represents the energy lower limit of the energy range k; and $E_{k+1}$ represents the energy upper limit of the energy range k.

Based on the charge sharing model, the energy resolution model and the pulse pileup model, the photon-counting model can be created through the above formulas (1) to (9).

In the actual detection process of the photon-counting detector, the physical effects such as charge sharing, energy resolution and pulse pileup are coupled to a certain extent. However, in the photon-counting model provided by examples of the present disclosure, the charge sharing, energy resolution and pulse pileup are mutually independent and continuously act on the energy spectrum, and the comprehensive effect is generated by model combination to adjust the material distribution parameter value.

In the above formulas (1) to (9), when the material distribution parameter value is the voxel attenuation coefficient, the material distribution parameter value can be expressed by the attenuation coefficient and mass density of each tissue component of the voxel. When the material distribution parameter value is a mass density, the target material distribution parameter value is a target mass density. The system uses the above formulas (1) to (9) to determine the target mass density of each voxel tissue component, and performs imaging according to the target mass density.

Performance Parameter Measurement of the Photon-Counting Detector

The photon-counting model can include multiple parameters, which are measured by experiments or according to the relevant physical parameters of the photon-counting model. For example, the performance parameters depended by the charge sharing model can include the size of the sub-detector, the intensity of the applied electric field, and the semiconductor transport characteristics. In the energy resolution model, the energy resolution can be measured. Combining energy correction results and the threshold traversal scan, the counting energy spectrum can be obtained. The full width at half maxima (FWHM) can be obtained by performing Gaussian fitting on the main peak. The performance parameter depended by the pulse pileup model can include the dead time. For the photon-counting detector, the dead time can be pre-calibrated and pre-configured. In the construction of the photon-counting model, the above relevant parameters can be measured.

Application of the Photon-Counting Model

In the application of the photon-counting model, the system obtains the photon-counting sequence $M_{ijk}$ output by the photon-counting detector after the CT scan on the subject is finished. The target material distribution parameter value is determined based on the photon-counting model shown in the above formula (9) and the photon-counting sequence $M_{ijk}$.

In some examples, by using the least square method, the target material distribution parameter value is determined based on the following formula (10):

$$\min \sum_{i=1}^{Q} \sum_{l=1}^{N} (N_{ijk} - M_{ijk})^2 \tag{10}$$

where $N_{ijk}$ represents the theoretical photon-counting sequence determined by the photon-counting model, $M_{ijk}$ represents the photon-counting sequence output by the photon-counting detector, Q represents the total number of scanning views, N represents the number of voxels obtained after dividing the subject, and K represents the serial number of the energy range.

Based on the formula (10), for each energy range, the material distribution parameter value in the photon-counting model is adjusted. When a difference between a theoretical photon-counting sequence and the photon-counting sequence is a minimum, the adjusted material distribution parameter value is determined as the target material distribution parameter value, where the theoretical photon-counting sequence is determined by the photon-counting model based on the adjusted material distribution parameter value. The system may perform imaging based on the target material distribution parameter value. Through the above solution, K images can be obtained, and one energy range corresponds to one image.

The system determines the target material distribution parameter value by the above iteration solution. The target material distribution parameter value is equal to or very close to the real material distribution parameter value, thereby ensuring the accuracy of the target material distribution parameter value.

In addition to the creation of the photon-counting model, performance parameter measurement of the photon-counting detector, and application of the photon-counting model, implementations of the present disclosure can further provide energy correction of the photon-counting detector.

According to the configured standard energy thresholds, each sub-detector counts incident photons in an energy range with a counter corresponding to the energy range of the sub-detector. After counting, each sub-detector outputs the photon-counting data of K different energy ranges. In some examples, assuming that the photon-counting detector supports simultaneous measurement of six energy ranges, the standard energy thresholds can be configured as 20 keV, 40 keV, 60 keV, 80 keV, 100 keV and 120 keV, respectively, so that the photon-counting detector can detect photon-counting data in six energy ranges (20, 40] keV, (40, 60] keV, (60, 80] keV, (80, 100] keV, (100, 120] keV, and (120, +∞] keV.

Each sub-detector can include a memory to store memory thresholds. Memory threshold is essentially energy threshold. The sub-detector counts photons in different energy ranges according to memory thresholds stored in memory.

Based on the structure and service life of the sub-detector, the performance of the sub-detector is different, and the detection results of the same standard energy threshold are different. In this case, if the memory is directly configured to store the standard energy threshold, the photon count data will be inaccurate due to the different performance of the sub-detector. For example, the standard energy threshold is 20 keV. Assuming that the structure of the first sub-detector and the second sub-detector are the same, the service time of the first sub-detector is longer than that of the second sub-detector, the memory in the first sub-detector stores the memory threshold of 20 keV, and the memory in the second sub-detector also stores the memory threshold value of 20 keV. In this case, when the first sub-detector counts photons, the first sub-detector may count photons with energy of 19.5 keV due to the performance difference, thereby resulting in the large photon count data.

To solve the above problems, a correction table can be predetermined, in which the correspondence between the standard energy threshold and the memory threshold of each sub-detector can be recorded. Before scanning, according to the standard energy threshold, the system can configure the corresponding memory threshold of each sub-detector with the correction table. The sub-detector counts the photons in different energy ranges based on the memory thresholds stored in the memory of the sub-detector, so as to implement the counting of the photons in energy ranges corresponding to the standard energy thresholds. After the system configured the memory thresholds, scanning on the subject can be started.

The correspondence in the correction table can be determined before the photon-counting detector is used or the correspondence in the correction table can be corrected periodically. Taking a linear model as an example, the correspondence between the standard energy threshold and the memory threshold is represented by the following formula (11):

$$E = G \cdot THR + b \quad (11)$$

where E represents the standard energy threshold; THR represents the memory threshold; G represents a gain; and b represents a bias. G and b are constants by correction. The gain G represents the change amount of energy threshold caused by one-unit change of memory threshold. Bias b refers to that when the memory threshold is 0, a real energy threshold is not 0. Due to the difference between sub-detectors, the G and b of each sub-detector are different, so the G and b of each sub-detector is separately determined to get the correction table.

The determination of G and b of the sub-detector can be performed with a radioisotope method or K-edge characteristics of materials. For example, the radioisotope method can include the following steps:

At a first step, with radioisotope A having known peak energy $E_A$ as a ray source, the memory threshold is set to the lowest (recorded as THR[0]), and the signals within time $\Delta t$ are continuously acquired to obtain a total photon count $N_A[0]$.

At a second step, the memory threshold is gradually increased by taking $\Delta THR$ as a threshold step length, and the first step is repeated to obtain the total photon count $N_A[s]$ (s is an integer from 0 to Z) corresponding to the memory threshold THR[s]=THR[0]+s·$\Delta THR$, where Z represents the number of repetitions of the first step.

At a third step, with radioisotope B having known peak energy $E_B$ as a ray source, the first and second steps are repeated to obtain a total photon count $N_B[s]$ (s is an integer from 0 to Z).

The difference quotients of the total photon count $N_A[s]$ and the total photon count $N_B[s]$ to the memory threshold can be respectively determined, a difference quotient-memory threshold curve can be drawn, and Gaussian fitting can be performed on the main peak range to obtain the memory threshold $THR_A$ and the memory threshold $THR_B$ corresponding to the peak energy.

The values of G and b can be obtained by introducing ($THR_A$, $E_A$) and ($THR_B$, $E_B$) into the above formula (11).

In examples provided by the present disclosure, various models related to the physical process of the photon-counting detector are combined in the image reconstruction process, so as to eliminate the artifacts caused by energy spectrum distortion and counting loss. The method provided in the present disclosure can be applied to the scanning processes such as tomography scanning, spiral scanning, and so on.

Corresponding to the above imaging methods, the present disclosure further provides examples of imaging apparatuses and image processing devices.

Figure 4:
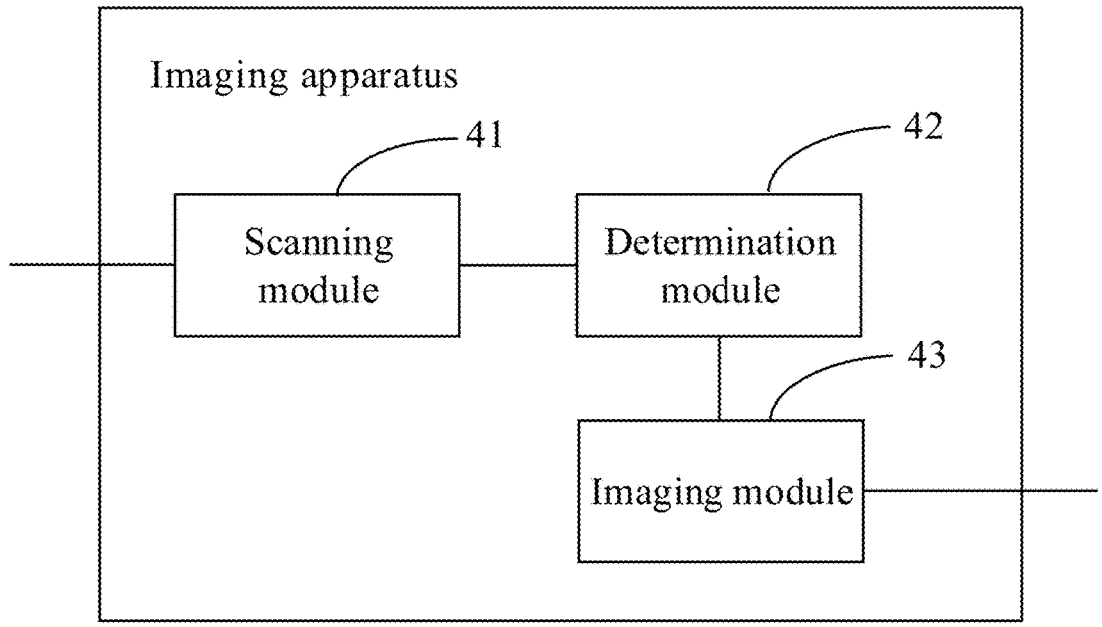
FIG. 4 is a functional module diagram of an imaging apparatus according to one or more examples of the present disclosure.

FIG. 4 is a functional module diagram of an imaging apparatus according to one or more examples of the present disclosure. The imaging apparatus is applied to a photon-counting CT system and includes a scanning module 41, a determination module 42 and an imaging module 43.

The scanning module 41 is configured to scan a subject to obtain a photon-counting sequence output by a photon-counting detector of the photon-counting CT system.

The determination module 42 is configured to determine, by using a photon-counting model and the photon-counting sequence, a target material distribution parameter value of the subject, the photon-counting model being created by at least one of a charge sharing model, an energy resolution model or a pulse pileup model, the charge sharing model being configured to eliminate energy spectrum distortion and counting loss caused by charge sharing, the energy resolution model being configured to eliminate energy spectrum distortion and counting loss caused by energy resolution, and the pulse pileup model being configured to eliminate energy spectrum distortion and counting loss caused by pulse pileup.

The imaging module 43 is configured to perform imaging based on the target material distribution parameter value.

In some examples, the determination module 42 is further configured to adjust a material distribution parameter value in the photon-counting model; in response to determining that a difference between a theoretical photon-counting sequence and the photon-counting sequence is a minimum, determine the adjusted material distribution parameter value as the target material distribution parameter value, wherein the theoretical photon-counting sequence is determined by the photon-counting model based on the adjusted material distribution parameter value.

In some examples, the determination module 42 is further configured to adjust a material distribution parameter value in the photon-counting model; in response to determining that a probability that a theoretical photon-counting sequence determined by the photon-counting model based on the adjusted material distribution parameter value is the photon-counting sequence is highest, determine the adjusted material distribution parameter value as the target material distribution parameter value.

In some examples, the imaging apparatus further includes an incident ray energy spectrum determining module configured to: determine a tube emission energy spectrum corresponding to an exposure voltage, an exposure current and an exposure time; and for each of sub-detectors of the photon-counting detector under each scanning view, determine an attenuation length of rays passing through a shape filter of the photon-counting CT system as a first attenuation length, wherein the rays enter into the sub-detector after passing through the subject under the scanning view; for each voxel of the subject, determine an attenuation length of the rays passing through the voxel as a second attenuation length; and determine an incident ray energy spectrum of the sub-detector under the scanning view based on the tube emission energy spectrum, the first attenuation length, each second attenuation length and a material distribution parameter value of each voxel.

In some examples, the imaging apparatus further includes photon-counting model creating module configured to: for each of the sub-detectors of the photon-counting detector under each scanning view, determine the charge sharing model based on the incident ray energy spectrum; determine the energy resolution model based on the charge sharing model; determine the pulse pileup model based on the energy resolution model; determine a counting energy spectrum based on the pulse pileup model; create the photon-counting model based on the counting energy spectrum.

Figure 5:
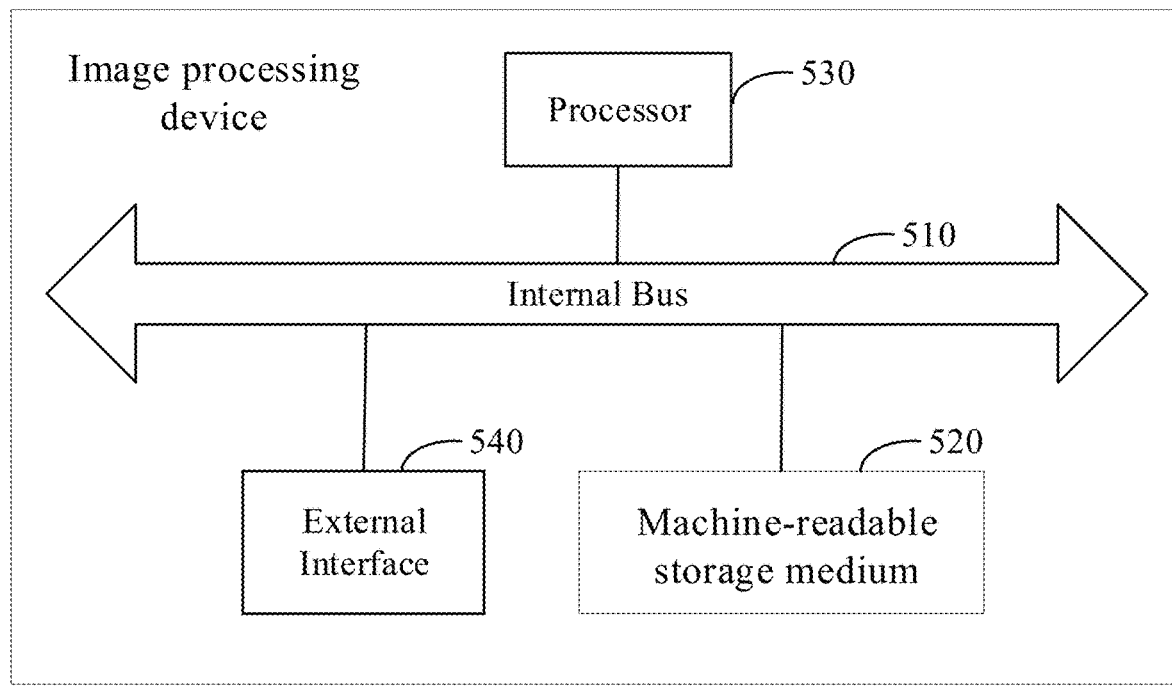
FIG. 5 is a schematic diagram of an image processing device according to one or more examples of the present disclosure.

FIG. 5 is a schematic diagram of an image processing device according to one or more examples of the present disclosure. The image processing device includes a machine-readable storage medium 520, a processor 530 and an external interface 540 coupled via an internal bus 510. The machine-readable storage medium 520 stores machine-executable instructions.

When executing the machine-executable instructions, the processor 530 is caused to perform operations including: obtaining a photon-counting sequence output by a photon-counting detector of the photon-counting CT system after a CT scan on a subject is finished; determining, by using a photon-counting model and the photon-counting sequence, a target material distribution parameter value of the subject, the photon-counting model being created by at least one of a charge sharing model, an energy resolution model or a pulse pileup model, the charge sharing model being configured to eliminate energy spectrum distortion and counting loss caused by charge sharing, the energy resolution model being configured to eliminate energy spectrum distortion and counting loss caused by energy resolution, and the pulse pileup model being configured to eliminate energy spectrum distortion and counting loss caused by pulse pileup; and performing imaging based on the target material distribution parameter value. The photon-counting detector communicates with the processor 530 through the external interface 540.

The operations further include steps described in the imaging methods provided by the above examples, which is not repeated herein. Specific details may refer to the imaging methods provided by the above examples.

In some examples, the machine-readable storage medium 520 may be in various forms. In different examples, the machine-readable storage medium 520 may include RAM (random access memory), volatile memory, non-volatile memory, flash memory, storage drive (such as hard disk drive), solid-state hard disk, any type of storage disk (such as CD, DVD, etc.), or similar storage media, or a combination of them. In particular, the machine-readable storage medium can also be paper or other suitable media capable of printing programs. With these media, these programs can be obtained electrically (e.g., optical scanning), compiled, interpreted, and processed in an appropriate manner, and then stored in computer media.

For simplicity and illustrative purposes, the present disclosure is described by referring mainly to examples thereof. In the above descriptions, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

The above description is merely preferred examples of the present disclosure and is not intended to limit the present disclosure in any form. Although the present disclosure is disclosed by the above examples, the examples are not intended to limit the present disclosure. Those skilled in the art, without departing from the scope of the technical scheme of the present disclosure, may make a plurality of changes and modifications of the technical scheme of the present disclosure by the method and technical content disclosed above.

Therefore, without departing from the scope of the technical scheme of the present disclosure, based on technical essences of the present disclosure, any simple alterations, equal changes and modifications should fall within the protection scope of the technical scheme of the present disclosure. Accordingly, other embodiments are within the scope of the following claims.

What is claimed is:

1. An imaging method, applied in a photon-counting CT system, the imaging method comprising:
scanning a subject to obtain a photon-counting sequence outputted by a photon-counting detector of the photon-counting CT system;
determining, by using a photon-counting model and the photon-counting sequence, a target material distribution parameter value of the subject, the photon-counting model being created by a charge sharing model, an energy resolution model, and a pulse pileup model, the charge sharing model being configured to eliminate energy spectrum distortion and counting loss caused by charge sharing, the energy resolution model being configured to eliminate energy spectrum distortion and counting loss caused by energy resolution, and the pulse pileup model being configured to eliminate energy spectrum distortion and counting loss caused by pulse pileup, wherein the charge sharing model is configured to, based on a first result output by an incident ray energy spectrum model, output a second result, the energy resolution model is configured to output a third result based on the second result output by the charge sharing model, the pulse pileup model is configured to output a fourth result based on the third result output by the energy resolution model, and the photon-counting model is configured to output a photon-counting result based on the fourth result output by the pulse pileup model; and
performing imaging based on the target material distribution parameter value.

2. The method of claim 1, wherein determining, by using the photon-counting model and the photon-counting sequence, the target material distribution parameter value of the subject comprises:
   adjusting a material distribution parameter value in the photon-counting model; and
   in response to determining that a difference between a theoretical photon-counting sequence and the photon-counting sequence is a minimum, determining the adjusted material distribution parameter value as the target material distribution parameter value, wherein the theoretical photon-counting sequence is determined by the photon-counting model based on the adjusted material distribution parameter value.

3. The method of claim 1, wherein determining, by using the photon-counting model and the photon-counting sequence, the target material distribution parameter value of the subject comprises:
   adjusting a material distribution parameter value in the photon-counting model; and
   in response to determining that a probability of a theoretical photon-counting sequence being the photon-counting sequence is highest, determining the adjusted material distribution parameter value as the target material distribution parameter value, wherein the theoretical photon-counting sequence is determined by the photon-counting model based on the adjusted material distribution parameter value.

4. The method of claim 1, further comprising:
   determining a tube emission energy spectrum corresponding to an exposure voltage, an exposure current, and an exposure time; and
   for each of sub-detectors of the photon-counting detector under each scanning view,
      determining an attenuation length of rays passing through a shape filter of the photon-counting CT system as a first attenuation length, wherein the rays enter into the sub-detector after passing through the subject under the scanning view;
      for each voxel of the subject, determining an attenuation length of the rays passing through the voxel as a second attenuation length; and
      determining an incident ray energy spectrum of the sub-detector under the scanning view based on the tube emission energy spectrum, the first attenuation length, and the second attenuation length and a material distribution parameter value of each voxel of the subject.

5. The method of claim 4, further comprising:
   for each of the sub-detectors of the photon-counting detector under each scanning view,
      determining the charge sharing model based on the incident ray energy spectrum;
      determining the energy resolution model based on the charge sharing model;
      determining the pulse pileup model based on the energy resolution model;
      determining a counting energy spectrum based on the pulse pileup model; and
      creating the photon-counting model based on the counting energy spectrum.

6. The method of claim 4, wherein the incident ray energy spectrum of the sub-detector under the scanning view is represented by:

$$S_{ij}(E_0)=S_0(E_0)\exp(-L_{ij}\mu_f(E_0)-\Sigma_{l=1}^{N}a_{ijl}\mu_l(E_0)),$$

where $S_{ij}(E_0)$ represents an incident ray energy spectrum of a j-th sub-detector under an i-th scanning view;
$E_0$ represents an energy of an incident photon;
$S_0(E_0)$ represents the tube emission energy spectrum corresponding to the exposure voltage, the exposure current and the exposure time;
i represents a serial number of the scanning view;
j represents a serial number of the sub-detector;
$\mu_f(E_0)$ represents an attenuation coefficient curve of the shape filter;
$L_{ij}$ represents the first attenuation length;
l represents a serial number of the voxel;
$a_{ijl}$ represents the second attenuation length;
$\mu_l(E_0)$ represents a material distribution parameter value of the voxel l; and
N represents a number of voxels obtained after dividing the subject.

7. The method of claim 6, wherein the charge sharing model is represented by:

$$S_{CS}(E_1)=\mathcal{F}_{CS}(S_{ij})=\int_0^{\infty}S_{ij}(E_0)R_{CS}(E_1|E_0)dE_0,$$

where $S_{CS}(E_1)$ represents a charge sharing distortion spectrum;
$E_1$ represents an energy of a detected photon under an effect of charge sharing;
$\mathcal{F}_{CS}$ represents a mapping relationship between $S_{ij}(E_0)$ and $S_{CS}(E_1)$; and
$R_{CS}(E_1|E_0)$ represents a response function of charge sharing energy spectrum.

8. The method of claim 7, wherein the energy resolution model is represented by:

$$S_{ER}(E_2)=\mathcal{F}_{ER}(S_{CS})=\int_0^{\infty}S_{CS}(E_1)R_{ER}(E_2|E_1)dE_1,$$

where $S_{ER}(E_2)$ represents an energy resolution spectrum;
$E_2$ represents an energy of the detected photon under an effect of energy resolution;
$\mathcal{F}_{ER}$ represents a mapping relationship between $S_{CS}(E_1)$ and $S_{ER}(E_2)$; and
$R_{ER}(E_2|E_1)$ represents a response function of the energy resolution spectrum.

9. The method of claim 8, wherein the pulse pileup model is represented by:

$$S_{PP}(E_3)=\mathcal{F}_{PP}(S_{ER})N_0(1-DLR)\Sigma_{m=0}^{M}P(m)\cdot\Omega(E_3|m,S_{ER}(E_2)),$$

where $S_{PP}(E_3)$ represents a pulse pileup distortion spectrum;
$E_3$ represents an energy of the detected photon under an effect of pulse pileup;
$\mathcal{F}_{PP}$ represents a mapping relationship between $S_{ER}(E_2)$ and $S_{PP}(E_3)$;
$N_0$ represents a total number of incident photons in the i-th scanning view;
DLR represents a count loss rate;
m represents an order of the pulse pileup;
M represents the maximum order of the pulse pileup under the i-th scanning view;
P(m) represents a probability that a counted event is an m-order pulse pileup under the i-th scanning view; and
$\Omega(E_3|m, S_{ER}(E_2))$ represents a spectral density function of the m-order pulse pileup.

10. The method of claim 9, wherein the photon-counting model is represented by:

$$N_{ijk} = \int_{E_k}^{E_{k+1}} \tilde{S}_{ij}(E_3) dE_3$$

$$\tilde{S}_{ij}(E_3) = \mathcal{F}[S_{PP}(E_3)],$$

where $\tilde{S}_{ij}(E_3)$ represents a counting energy spectrum recorded by the j-th sub-detector under the i-th scanning view;
$\mathcal{F}$ represents a mapping relationship between $S_{pp}(E_3)$ and $\tilde{S}_{ij}(E_3)$;
$N_{ijk}$ represents a number of detected photons within an energy range $E_k$ to $E_{k+1}$ detected by the j-th sub-detector under the i-th scanning view;
k represents a serial number of the energy range;
$E_k$ represents an energy lower limit of the energy range k; and
$E_{k+1}$ represents an energy upper limit of the energy range k.

11. The method of claim 1, wherein the target material distribution parameter value comprises one of:
a target voxel attenuation coefficient; and
a target mass density of voxel tissue component.

12. The method of claim 1, further comprising:
for each of sub-detectors of the photon-counting detector, performing energy correction on a memory threshold stored in a memory of the sub-detector using a predetermined correction table, wherein the sub-detector is configured to count photons with the memory threshold.

13. A device comprising:
at least one processor; and
at least one non-transitory machine-readable storage medium coupled to the at least one processor having machine-executable instructions stored thereon that, when executed by the at least one processor, cause the at least one processor to perform operations comprising:
obtaining a photon-counting sequence output by a photon-counting detector of a photon-counting CT system after a CT scan on a subject is finished;
determining, by using a photon-counting model and the photon-counting sequence, a target material distribution parameter value of the subject, the photon-counting model being created by a charge sharing model, an energy resolution model, and a pulse pileup model, the charge sharing model being configured to eliminate energy spectrum distortion and counting loss caused by charge sharing, the energy resolution model being configured to eliminate energy spectrum distortion and counting loss caused by energy resolution, and the pulse pileup model being configured to eliminate energy spectrum distortion and counting loss caused by pulse pileup, wherein the charge sharing model is configured to, based on a first result output by an incident ray energy spectrum model, output a second result, the energy resolution model is configured to output a third result based on the second result output by the charge sharing model, the pulse pileup model is configured to output a fourth result based on the third result output by the energy resolution model; and the photon-counting model is configured to output a photon-counting result based on the fourth result output by the pulse pileup model; and
performing imaging based on the target material distribution parameter value.

14. The device of claim 13, wherein determining, by using the photon-counting model and the photon-counting sequence, the target material distribution parameter value of the subject comprises:
adjusting a material distribution parameter value in the photon-counting model; and
in response to determining that a difference between a theoretical photon-counting sequence and the photon-counting sequence is a minimum, determining the adjusted material distribution parameter value as the target material distribution parameter value, wherein the theoretical photon-counting sequence is determined by the photon-counting model based on the adjusted material distribution parameter value.

15. The device of claim 13, wherein determining, by using the photon-counting model and the photon-counting sequence, the target material distribution parameter value of the subject comprises:
adjusting a material distribution parameter value in the photon-counting model; and
in response to determining that a probability of a theoretical photo-counting sequence being the photon-counting sequence is highest, determining the adjusted material distribution parameter value as the target material distribution parameter value, wherein the theoretical photon-counting sequence is determined by the photon-counting model based on the adjusted material distribution parameter value.

16. The device of claim 13, wherein the operations further comprise:
determining a tube emission energy spectrum corresponding to an exposure voltage, an exposure current and an exposure time; and
for each of sub-detectors of the photon-counting detector under each scanning view,
determining an attenuation length of rays passing through a shape filter of the photon-counting CT system as a first attenuation length, wherein the rays enter into the sub-detector after passing through the subject under the scanning view;
for each voxel of the subject, determining an attenuation length of the rays passing through the voxel as a second attenuation length; and
determining an incident ray energy spectrum of the sub-detector under the scanning view based on the tube emission energy spectrum, the first attenuation length, each second attenuation length and a material distribution parameter value of each voxel.

17. The device of claim 16, wherein the operations further comprise:
for each of the sub-detectors of the photon-counting detector under each scanning view,
determining the charge sharing model based on the incident ray energy spectrum;
determining the energy resolution model based on the charge sharing model;
determining the pulse pileup model based on the energy resolution model;
determining a counting energy spectrum based on the pulse pileup model; and
creating the photon-counting model based on the counting energy spectrum.

18. The device of claim 13, wherein the target material distribution parameter value comprises one of:
- a target voxel attenuation coefficient; and
- a target mass density of voxel tissue component.

19. The device of claim 13, wherein the operations further comprise:
- for each of sub-detectors of the photon-counting detector, performing energy correction on a memory threshold stored in a memory of the sub-detector using a predetermined correction table, wherein the sub-detector is configured to count photons with the memory threshold.

20. An imaging method, applied in a photon-counting CT system, the imaging method comprising:
- scanning a subject to obtain a photon-counting sequence outputted by a photon-counting detector of the photon-counting CT system;
- determining a tube emission energy spectrum corresponding to an exposure voltage, an exposure current, and an exposure time;
- for each of sub-detectors of the photon-counting detector under each scanning view,
    - determining an attenuation length of rays passing through a shape filter of the photon-counting CT system as a first attenuation length, wherein the rays enter into the sub-detector after passing through the subject under the scanning view;
    - for each voxel of the subject, determining an attenuation length of the rays passing through the voxel as a second attenuation length; and
    - determining an incident ray energy spectrum of the sub-detector under the scanning view based on the tube emission energy spectrum, the first attenuation length, and the second attenuation length and a material distribution parameter value of each voxel of the subject;
- determining, by using a photon-counting model and the photon-counting sequence, a target material distribution parameter value of the subject, the photon-counting model being created by at least one of a charge sharing model, an energy resolution model, or a pulse pileup model, the charge sharing model being configured to eliminate energy spectrum distortion and counting loss caused by charge sharing, the energy resolution model being configured to eliminate energy spectrum distortion and counting loss caused by energy resolution, and the pulse pileup model being configured to eliminate energy spectrum distortion and counting loss caused by pulse pileup; and
- performing imaging based on the target material distribution parameter value.

* * * * *